United States Patent
Guittet et al.

(10) Patent No.: US 7,262,837 B2
(45) Date of Patent: Aug. 28, 2007

(54) NONINVASIVE METHOD FOR CHARACTERIZING AND IDENTIFYING EMBEDDED MICROPATTERNS

(75) Inventors: Pierre-Yves Guittet, Dresden (DE); Ulrich Mantz, Dresden (DE); Eckhard Marx, Radeburg (DE)

(73) Assignee: Infineon Technologies AG, Munich (DE)

( * ) Notice: Subject to any disclaimer, the term of this patent is extended or adjusted under 35 U.S.C. 154(b) by 349 days.

(21) Appl. No.: 10/877,262

(22) Filed: Jun. 25, 2004

(65) Prior Publication Data

US 2005/0018171 A1 Jan. 27, 2005

(30) Foreign Application Priority Data

Jul. 21, 2003 (DE) .................... 103 33 119

(51) Int. Cl.
*G01N 1/00* (2006.01)

(52) U.S. Cl. .................. 356/38; 356/601

(58) Field of Classification Search .................. 356/38, 356/600, 342, 432, 601
See application file for complete search history.

(56) References Cited

U.S. PATENT DOCUMENTS

| 6,233,046 | B1 | 5/2001 | Alba et al. | |
| 2002/0180986 | A1* | 12/2002 | Nikoonahad et al. | 356/600 |
| 2003/0058443 | A1* | 3/2003 | Xu et al. | 356/369 |

FOREIGN PATENT DOCUMENTS

JP     EP 1 253 418 A2     10/2002

* cited by examiner

*Primary Examiner*—Gregory J Toatley, Jr.
*Assistant Examiner*—Tri Ton
(74) *Attorney, Agent, or Firm*—Jenkins, Wilson, Taylor & Hunt, P.A.

(57) ABSTRACT

The invention relates to a method for noninvasively characterizing embedded micropatterns which are hidden under the surface of a wafer down to 100 μm. The micropatterns are identified with reference micropatterns from a previously produced reference library with the aid of their specific ellipsometric parameters.

7 Claims, 2 Drawing Sheets

NONINVASIVE METHOD FOR CHARACTERIZING AND IDENTIFYING EMBEDDED MICROPATTERNS

TECHNICAL FIELD

The invention relates to a noninvasive method for characterizing embedded micropatterns whose critical dimensions (CD) are between 10 μm and 100 μm in particular.

BACKGROUND ART

Embedded micropatterns are used in so-called microelectromechanical systems (MEMS), in which mechanical and electronic components are combined as a component on a substrate. Such MEMS form inertia sensors, gas sensors and micromotors, for example. FIG. 1 shows a diagram of the design of an embedded micropattern with irregular depth profile. The spacing between the basic structure, mostly consisting of silicon, and the surface can be a few hundred μm. The structures also frequently have cavities, or are constructed from different materials.

There are currently no non-destructive methods for characterizing the irregular depth structures of embedded micropatterns which can be used during the production process. The determination of the structure of embedded micropatterns by means of scanning atomic force microscopy (AFM) is, on the one hand, very slow and, on the other hand, severely limited with reference to the determination of the depth of the micropatterns, because deep lying cavities or very irregular depth profiles are inaccessible from the surface. This also holds for the use of the scanning electron microscope (SEM) or the scanning tunneling microscope (STM) whose use additionally destroys the micropattern to be characterized. Procedures based on spectroscopic methods are certainly not destructive, but are limited to the determination of relatively simple patterns on the surface or homogeneous film layers on substrates, because the light normally used for spectroscopy does not penetrate into the regions of the embedded micropatterns of up to 100 μm in depth.

Planar layer systems can be characterized by means of scattered light analysis. The method of ellipsometry, which constitutes a specific form of reflection spectroscopy, is particularly suitable. U.S. Pat. No. 5,910,842 describes a method and a device for determining so-called ellipsometric data of, for example, thin layers on a substrate. Ellipsometry is concerned with the change in the state of polarization of the light during the reflection or scattering of polarized light at a periodically structured surface. FIG. 2 shows a spectrometer S according to the prior art. Here, polarized light is focused from a light source 1 through the polarizer 2 and a focusing unit 3 onto a surface by which it is scattered. The scattered light is reflected onto a detector D via a focusing unit F and the analyzer An. For a given wavelength λ and a fixed angle of incidence φ which is illustrated in FIG. 3, the so-called ellipsometric parameters α(λ) and β(λ) and ψ(λ) and Δ(λ) can be determined from the intensities, determined by the detector D, of the scattered light I(λ, σ) for a given number of polarization planes σ which are determined by the analyzer An;

$$\alpha(\lambda) = \frac{I(\lambda, 0°) - I(\lambda, 90°)}{I(\lambda, 0°) + I(\lambda, 90°)}, \quad (1)$$

$$\beta(\lambda) = \frac{I(\lambda, 45°) - I(\lambda, 135°)}{I(\lambda, 45°) + I(\lambda, 135°)}$$

$$\tan\psi = \tan\sigma \frac{\sqrt{1-\alpha}}{\sqrt{1+\alpha}}, \quad (2)$$

$$\cos\Delta = \frac{\beta}{1-\alpha^2}$$

In the UV/VIS region, the optical constants, specifically the refractive index n and the absorption coefficient k as well as the layer thickness as far as sub-monolayers of atoms and/or molecules of the surface can be determined from the intensities by means of ellipsometric analysis.

SUMMARY OF THE INVENTION

It is therefore an object of the present invention to create a quick, noninvasive method for characterizing embedded micropatterns with complicated depth profiles made from different materials, which can be employed flexibly and in as automated a way as possible in the production cycle.

This object is achieved according to the invention by means of the method specified in claim 1.

Advantageous developments and improvements of the method specified in claim 1 are to be found in the subclaims.

In accordance with a preferred development, the spectroscopy is performed in the infrared wavelength region from λ=1.4 μm to 16 μm, for which the silicon substrate is transparent.

In accordance with a further preferred development, the reference data records are generated by recording intensity spectra at wafers which contain embedded micropatterns with known depth profiles, and calculating the ellipsometric parameters and outputting them into a data record reference data record.

In accordance with a further preferred development, the reference data records are generated by means of Rigorous Coupled Wave Analysis (RCWA) with the aid of model micropatterns with known depth profiles. In this case, the structural properties of the micropatterns are constructed in layers in a model, and the solution of the Maxwell equations is calculated numerically in order to determine the ellipsometric parameters to be expected in the case of infrared reflection spectroscopy.

In accordance with a further preferred development, the metrical distance between the data record including the measured ellipsometric parameters and the reference library data records is selected as correspondence criterion.

In accordance with a further preferred development, the wafer is classified as defective or intact with the aid of the degree of correspondence between the data record including the measured ellipsometric parameters and a predetermined reference data record from the reference library of the wafers containing the embedded micropatterns.

In accordance with a further preferred development, the degree of correspondence between the data record including the measured ellipsometric parameters and a reference data record is the metric distance.

The method according to the invention for characterizing embedded micropatterns offers the advantage that it is quick and noninvasive. The spectra for calculating the ellipsometric parameters can be recorded during the fabrication process of the wafers which contain the embedded micropatterns, and the micropatterns be identified and characterized during the production cycle.

BRIEF DESCRIPTION OF THE DRAWING

Exemplary embodiments of the invention are illustrated in the drawings and explained in the following description.

DETAILED DESCRIPTION OF THE INVENTION

Identical reference symbols denote identical or functionally identical components in the figures.

On the basis of infrared ellipsometry, an exemplary embodiment provides a method which characterizes the depth profiles of embedded micropatterns below the surface.

Figure 4:
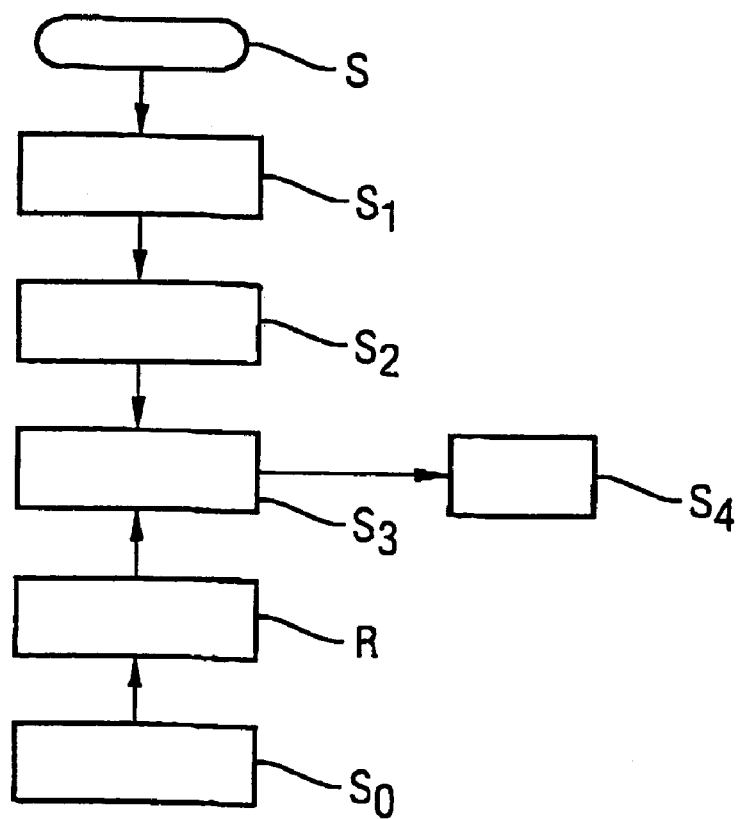
FIG. 4 shows a flowchart of the method according to the invention with its method steps.

The method steps of the exemplary embodiment are combined in a flowchart in FIG. 4. In the first step S1, the ellipsometric parameters of a region on the wafer to be examined are determined.

Figure 1:
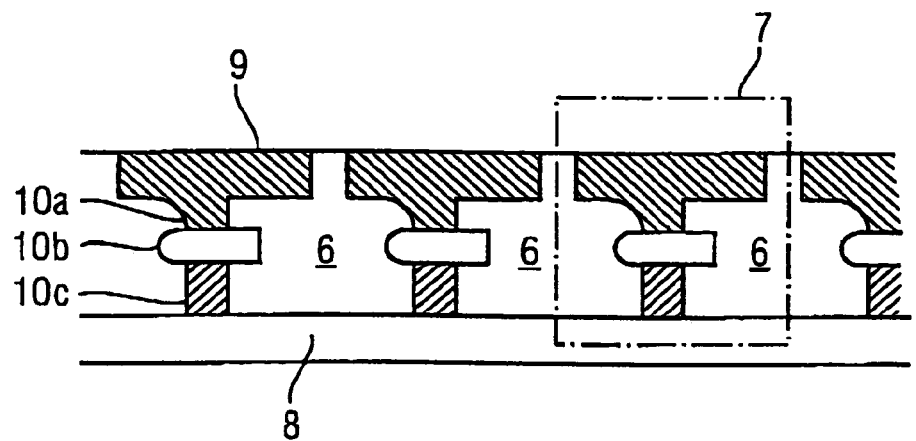
FIG. 1 shows the typical design of an embedded micropattern on a wafer.

The patterns to be inspected are located on silicon wafers, as a rule, and have critical dimensions CD of 10 μm to 100 μm. FIG. 1 shows such a depth profile 7 on a substrate 8. The embedded micropattern in FIG. 1 also has cavities 6, and is constructed from different materials 10a-10c. The spacing between the surface 9 and the basic substrate 8 can be a few hundred μm.

Figure 2:
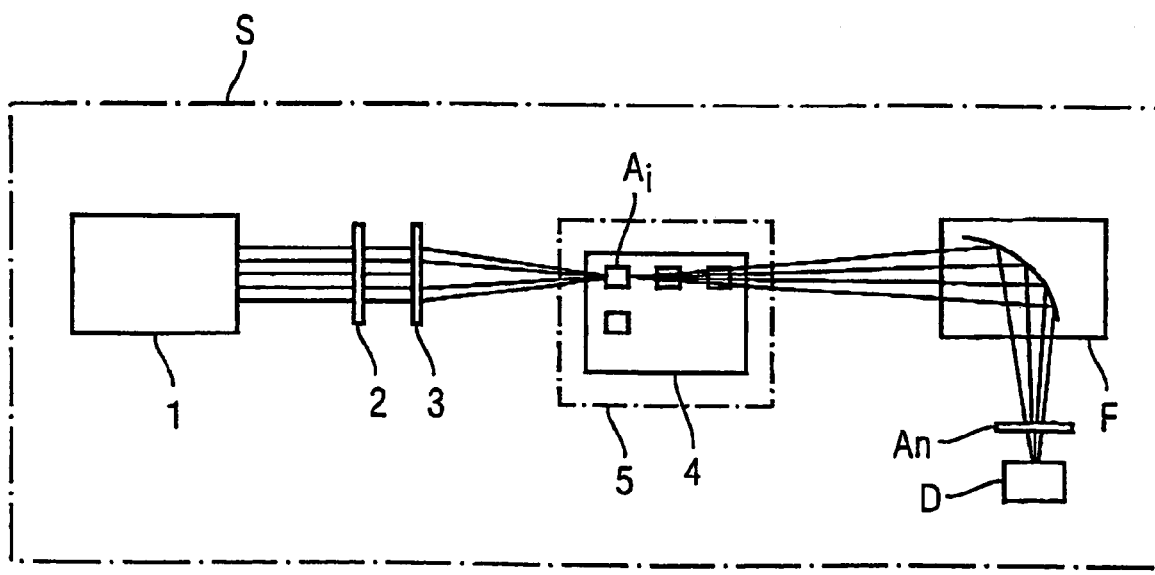
FIG. 2 shows a spectrometer for ellipsometry according to the prior art.
Figure 3:
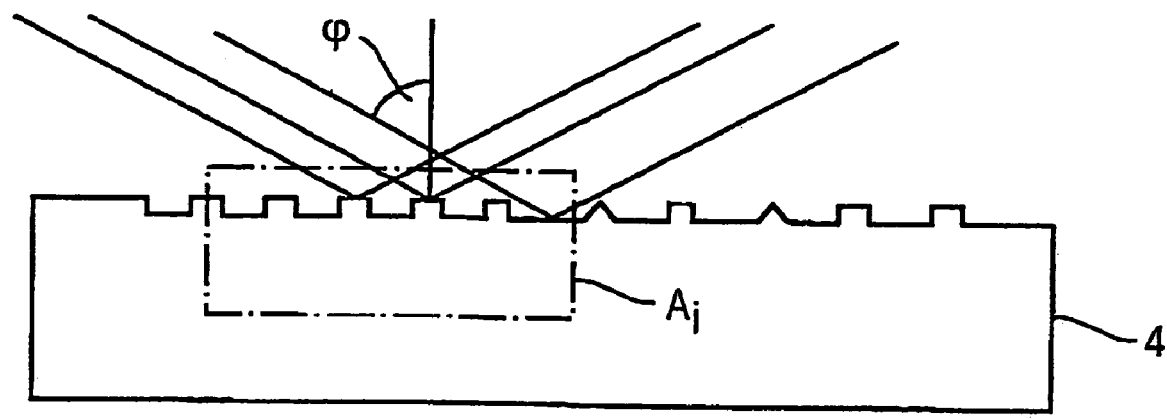
FIG. 3 shows a two-dimensional region of a wafer and the angle of incidence.

Intensity spectra of a number of predetermined two-dimensional regions $A_i$ on this wafer 4 are recorded together with a predetermined number of angles of incidence $\phi$ with the aid of a conventional spectrometer S as described in FIG. 2. FIG. 3 shows such a predetermined region $A_i$ on a wafer 4 and the angle of incidence $\phi$. In a particularly preferred development, the wafer 4 to be examined is mounted on an xyz stage 5 which is used to bring the two-dimensional regions $A_i$ into the focus of the polarized light. The two-dimensional regions can be, for example, 5 ellipses of magnitude 80 μm×300 μm defined on the surface.

The ellipsometric parameters $\psi(\lambda)$ and $\Delta(\lambda)$ for the two-dimensional regions $A_i$ and the angles of incidence $\phi$ are calculated from the measured intensities using equation (2) (step S1), and stored in a data record D (step S2). In this way, a specific wafer is assigned a specific data record which includes the ellipsometric parameters $\psi$ and $\Delta$ for the respective wavelength region, angles of incidence $\phi$ and the regions $A_i$.

This data record D is compared in step S3 with all the data records $R_i$ from a reference library R, and the reference data record $R_i$ which corresponds most highly to the data record D is output (step S4).

The reference data records $R_i$ which form the reference library R and in each case correspond to a micropattern with a known depth profile, of known material composition, are generated using a specific method (step S0). In a particular exemplary embodiment of the method according to the invention, the reference data records $R_i$ are generated by determining the ellipsometric parameters of wafers with known micropatterns in accordance with step S1 and storing them in a data record $R_i$.

As soon as the reference data record $R_i$ which corresponds most highly to the data record is found, the embedded micropattern on the wafer is identified with the micropattern corresponding to the reference data record $R_i$. In a preferred development, the parameters or data associated with a wafer are arranged in a vector, and the degree of correspondence between the reference data records and the data record D originating to be examined is the metric distance in the parameter space. The smaller the metric distance, the higher the degree of correspondence.

LIST OF REFERENCE SYMBOLS

1 Light source
2 Polarizer
3 Focusing device
4 Wafer with embedded micropatterns
5 xyz stage
6 Cavity
7 Depth profile
8 Substrate
9 Surface
10a Material layer
10b Material layer
10c Material layer
$A_i$ Specific region on wafer
F Focusing unit
An Analyzer
D Detector
S Spectrometer
$\phi$ Angle of incidence

DESIGNATION OF THE METHOD STEPS $S_0$: Production of reference data records $R_1 \ldots R_N$
$S_1$: Calculating the ellipsometric parameters $\psi(\lambda)$ and $\Delta(\lambda)$
$S_2$: Outputting the $\psi(\lambda)$ and $\Delta(\lambda)$ in data record D
$S_3$: Comparing and identifying with reference data $R_1$ from reference library R
$S_4$: Outputting the most highly corresponding $R_i$
R: Reference library

The invention claimed is:

1. Method for characterizing embedded microstructures with critical dimensions of between 10 μm and 100 μm, the method comprising:

(a) providing polarized light,
(b) focusing the polarized light onto a predetermined two-dimensional region from a predetermined number of two-dimensional regions at a predetermined number of angles on a wafer which contains the embedded microstructures,
(c) focusing the light, scattered by the respective region on the wafer, onto a detector with the aid of a focusing unit,
(d) interposing a polarization filter between the focusing unit and the detector,
(e) recording intensity spectra for a specific number of polarization planes, angles of incidence and a specific wavelength region,
(f) calculating the ellipsometric parameters $\Psi$ and $\Delta$ for a specific wavelength region,
(g) determining the ellipsometric parameters after the method steps (a)-(f) for the remaining predetermined two-dimensional regions of the wafer, (h) storing the ellipsometric parameters Ψ and Δ for the specific number of angles φ and the two-dimensional regions of the wafer in a data record, (i) comparing the data record with the predetermined reference data records from a reference data library, and (j) determining the reference data record which corresponds most highly to the data record in accordance with a predetermined criterion for providing characterization of embedded microstructures to a database, wherein the most highly corresponding reference data record is that which has the smallest metric distance on the measured data record.

2. Method according to claim 1, wherein spectra are recorded in the wavelength region between $\lambda=1.4\text{-}16$ μm.

3. Method according to claim 1 wherein the reference data records of the reference data library are generated in the following steps of
(a) providing a wafer with a test micropattern of known depth profile,
(b) determining a data record using the method steps (a)-(g) in accordance with claim 1, and
(c) storing the ellipsometric parameters ψ and Δ for the specific number of angles φ and the regions of the wafer in a reference data record.

4. Method according to claim 1 wherein the data records of the reference library are generated by means of RCWA on wafers with model micropatterns with known depth profiles.

5. Method according to claim 1, wherein the embedded micropatterns are constructed from layers of different materials.

6. Method according to claim 1, wherein the number of the spectroscoped two-dimensional regions is 5, 9 or 49, and they always have an ellipse of magnitude 80 μm×300 μm.

7. Method for characterizing embedded microstructures with critical dimensions of between 10 μm and 100 μm, the method comprising:
(a) providing polarized light;
(b) focusing the polarized light onto a predetermined two-dimensional region from a predetermined number of two-dimensional regions at a predetermined number of angles on a wafer which contains the embedded microstructures;
(c) focusing the light, scattered by the respective region on the wafer, onto a detector with the aid of a focusing unit;
(d) interposing a polarization filter between the focusing unit and the detector;
(e) recording intensity spectra for a specific number of polarization planes, angles of incidence and a specific wavelength region;
(f) calculating the ellipsometric parameters Ψ and Δ for a specific wavelength region;
(g) determining the ellipsometric parameters after the method steps (a)-(f) for the remaining predetermined two-dimensional regions of the wafer;
(h) storing the ellipsometric parameters Ψ and Δ for the specific number of angles φ and the two-dimensional regions of the wafer in a data record;
(i) comparing the data record with the predetermined reference data records from a reference data library; and
(j) determining the reference data record which corresponds most highly to the data record in accordance with a predetermined criterion for providing characterization of embedded microstructures to a database, wherein the wafer is classified as defective or intact with the aid of the degree of correspondence in accordance with a specific criterion between the data record and a predetermined reference data record, and wherein the degree of correspondence is given by the metric distance.

* * * * *